(12) United States Patent
Ito

(10) Patent No.: US 7,892,847 B2
(45) Date of Patent: Feb. 22, 2011

(54) METHOD AND APPARATUS FOR COUNTERCURRENT CHROMATOGRAPHY

(75) Inventor: Yoichiro Ito, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1349 days.

(21) Appl. No.: 10/509,697

(22) PCT Filed: Mar. 25, 2003

(86) PCT No.: PCT/US03/09189

§ 371 (c)(1),
(2), (4) Date: Jun. 6, 2005

(87) PCT Pub. No.: WO03/087807

PCT Pub. Date: Oct. 23, 2003

(65) Prior Publication Data

US 2005/0242040 A1    Nov. 3, 2005

(51) Int. Cl.
*B01D 15/08* (2006.01)
*B07B 7/00* (2006.01)

(52) U.S. Cl. .............. 436/161; 210/198.2; 210/198.3; 210/656; 210/658; 165/96; 165/152; 165/163; 165/166; 165/167; 165/174

(58) Field of Classification Search .............. 210/635, 210/638, 198.2, 198.3; 436/161; 165/96, 165/152, 163, 166, 167, 174
See application file for complete search history.

(56) References Cited

U.S. PATENT DOCUMENTS

| 4,414,108 | A | * | 11/1983 | Ito .......................... 210/198.2 |
| 4,430,216 | A | | 2/1984 | Ito |
| 4,551,251 | A | | 11/1985 | Kolobow et al. |
| 4,932,467 | A | * | 6/1990 | Wigmore et al. ............. 165/96 |
| 4,968,428 | A | * | 11/1990 | Nunogaki ................... 210/635 |

FOREIGN PATENT DOCUMENTS

JP    61-288154    12/1986

OTHER PUBLICATIONS

Degenhardt, A. et al. 2001 "Evaluation of different tubing geometries for high-speed countercurrent chromatography" *J. Chromatogr. A* 922:355-358.

* cited by examiner

*Primary Examiner*—Krishnan S Menon
*Assistant Examiner*—Rebecca Fritchman
(74) *Attorney, Agent, or Firm*—Polsinelli Shughart PC; Teddy C. Scott, Jr.; Paul A. Jenny

(57) ABSTRACT

A countercurrent chromatography apparatus includes a plurality of plates, at least one plate (16) having first and second interleaved spiral flow channels (52, 54, 56, 58) therein. Each spiral flow channels (52, 54, 56, 58) has a first end ($I_1, I_2, I_3, I_4$) near the central axis and a second ends ($O_1, O_2, O_3, O_4$) near the periphery. The outlet of the first channel ($O_1$) is connected to the inlet of the second channel ($I_2$) by a connecting channel (72). Septa may be provided between the plates to connect the spiral channels of one plate to the spiral channels of the next plate.

15 Claims, 8 Drawing Sheets

SEPARATION DISK WITH 4 SPIRAL CHANNELS

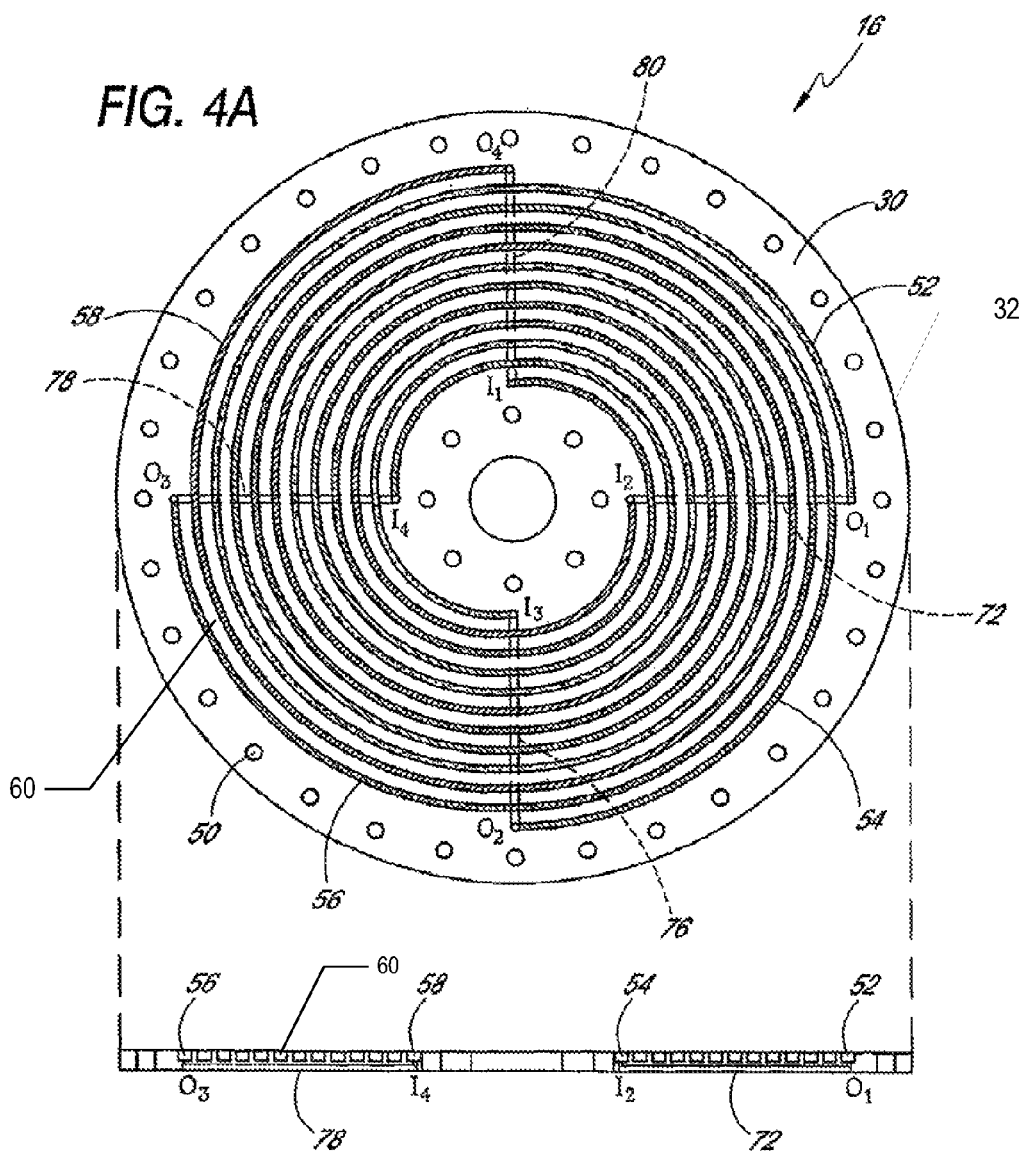

METHOD AND APPARATUS FOR COUNTERCURRENT CHROMATOGRAPHY

BACKGROUND OF THE INVENTION

1. Field of the Invention

The invention relates to countercurrent chromatography systems, and more particularly to an improved column design for use in countercurrent chromatography.

2. Description of the Related Art

Chromatography is a separation process that is achieved by distributing the substances to be separated between a mobile phase and a stationary phase. Those substances distributed preferentially in the moving phase pass through the chromatographic system faster than those that are distributed preferentially in the stationary phase. As a consequence, the substances are eluted from the column in inverse order of their distribution coefficients with respect to the stationary phase.

Chromatography is widely used for the separation, identification, and determination of the chemical components in complex mixture. Chromatographic separation can be utilized to separate gases, volatile substances, nonvolatile material, and polymeric material including biological substances.

The performance of countercurrent chromatography systems depends largely on the amount of stationary phase retained in the column, which determines both the resolving power of the solute peaks and the sample loading capacity. Numerous countercurrent chromatography systems have been developed to optimize the retention of the stationary phase of a sample in the column. The maximum attainable retention level tends to fall sharply with the application of higher flow rates of the mobile phase, resulting in loss of peak resolution. Consequently, the applicable flow rate has become one of the major limiting factors in countercurrent chromatography.

Some countercurrent chromatography systems utilize a complex hydrodynamic motion in two solvent phases within a column comprising a rotating coiled tube. If, for example, a horizontally mounted coil is filled with water and is rotated around its own axis, any object, either heavier or lighter than the water present in the column will tend to move toward one end of the coil. This end is then called the "head" and the other end, the "tail" of the coil. When the coil is filled with two immiscible solvent phases, the rotation establishes a hydrodynamic equilibrium between the two solvent phases, where the two phases are distributed in each turn at a given volume ratio (equilibrium volume ratio) and any excess of either phase remains at the tail of the coil.

When one of the solvent phases is added to the coil at its tail end and is further eluted from the coil at its head end, the hydrodynamic equilibrium tends to maintain the original equilibrium volume ratio of the two phases in the coil and thereby a certain volume of the other phase is permanently retained in the coil while the two phases are undergoing vigorous agitation with rotation of the coil. As a result, the sample solutes present in one phase and introduced locally at the inlet of the coil are subjected to an efficient partition process between the two phases and are chromatographically separated according to their partition coefficients.

In some cases, countercurrent chromatography utilizes a multi-layer coil as a separation column to produce a high efficiency separation with relatively favorable retention of the stationary phase in many solvent systems. Thus, countercurrent chromatography has been employed to achieve efficient extraction of a sample solution under relatively high flow rates. Previous column designs have relied on the use of a helical coil of tubing. U.S. Pat. No. 4,430,216, hereby incorporated by reference in its entirety, describes a preparative countercurrent chromatography utilizing a multiple layer coiled column. The coiled column design includes a length of plastic tubing wound around a coil holder to form multiple layers of the coil. Although this system works reasonably well for some solvents, these systems often fail to retain a satisfactory amount of the stationary phase for highly viscous, low interfacial solvent systems such as polymer phase systems, which are useful for the separation of macromolecules and particulates. In addition, the coiled tubing configuration is difficult to assemble, and connecting the ends of neighboring spiral tubing is rather difficult.

SUMMARY OF THE INVENTION

In one embodiment, the invention comprises a countercurrent chromatography apparatus comprising a plurality of plates, wherein at least one of the plurality of plates comprises at least first and second interleaved spiral flow channels formed therein. Each of the spiral flow channels includes a first end and a second end, wherein the first ends are closer to a central axis of the plate than the second ends, and wherein the second end of the first spiral flow channel is in fluid communication with the first end of the second spiral flow channel. The apparatus may additionally comprise a plurality of septa positioned between pairs of the plates, wherein at least some of the plurality of septa comprise a hole which is positioned to establish a fluid connection between a second end of a spiral flow channel in one of the plurality of plates and a first end of a spiral flow channel in a second of the plurality of plates.

In another embodiment, a countercurrent chromatography apparatus comprises a column assembly, wherein the column assembly comprises a plurality of coupled separation disks, and wherein each of the separation disks comprises at least two interleaved spiral flow channels.

In another embodiment, a plate for use in countercurrent chromatography comprises a first surface, a second opposed surface, and a plurality of interleaved spiral flow channels, each having an inner end and an outer end. At least one flow path connects an outer end of at least one of the spiral flow channels to an inner end of a different one of the interleaved spiral flow channels.

Methods of performing chromatography are also provided. In one embodiment, the method comprises routing fluid in a first groove from an inner end to an outer end of a first spiral flow path, routing the fluid in a second groove from the outer end of the first spiral flow path to an inner end of a third groove, and routing fluid in the third groove from an inner end to an outer end of a second spiral flow path.

BRIEF DESCRIPTION OF THE DRAWINGS

FIG. 4A is a top view of a separation disk having a plurality of spiral channels.

FIG. 4B is a cross section of the separation disk of FIG. 4A.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Although embodiments of the invention have various applications, many advantageous embodiments of the present invention are directed to an improved apparatus for use in countercurrent chromatography. Applicable chromatography techniques include those using synchronous planetary motion such as X-type, J-type, and I-type chromatography. The apparatus and methods described herein are especially advantageous when applied to high-speed countercurrent chromatography (HSCCC) with high flow rates. The column design may also be employed in large column applications for industrial-scale separations of samples by mounting the column assembly on a slowly rotating horizontal shaft. Some aspects of the invention are based, in part, on the surprising discovery that the retention of the stationary phase is improved if the configuration of the column used in countercurrent chromatography is modified from coiled tubing to a series of grooved plates (also referred to herein as separation disks) forming a plurality of interleaved spiral channels. The centrifugal force gradient produced by the spiral pitch in the separation disks helps to more efficiently distribute the heavier phase in the periphery and the lighter phase in the proximal portion of the column.

This centrifugal force effect on a sample is enhanced by increasing the pitch of the spiral, and a spiral column assembly prepared by simply winding tubing into a flat spiral configuration like thread on a spool provides only a limited spiral pitch. In accordance with these observations, a column for use in high speed countercurrent chromatography has been developed having interleaving, grooved separation disks with multiple flow channels instead of coiled tubing. The use of a column having interleaving, grooved separation disks has many advantages over the prior art. First, a column possessing a plurality of interleaving, grooved separation disks with multiple flow channels provides a greater spiral pitch than previous column designs, facilitating the movement of a fluid sample radially outward at a faster rate than with previous designs, thereby providing a more efficient separation of the two phases of a fluid sample. Finally, the column design of the present invention obviates the shortcomings of earlier column designs inasmuch as it is easier to manufacture.

Figure 1:
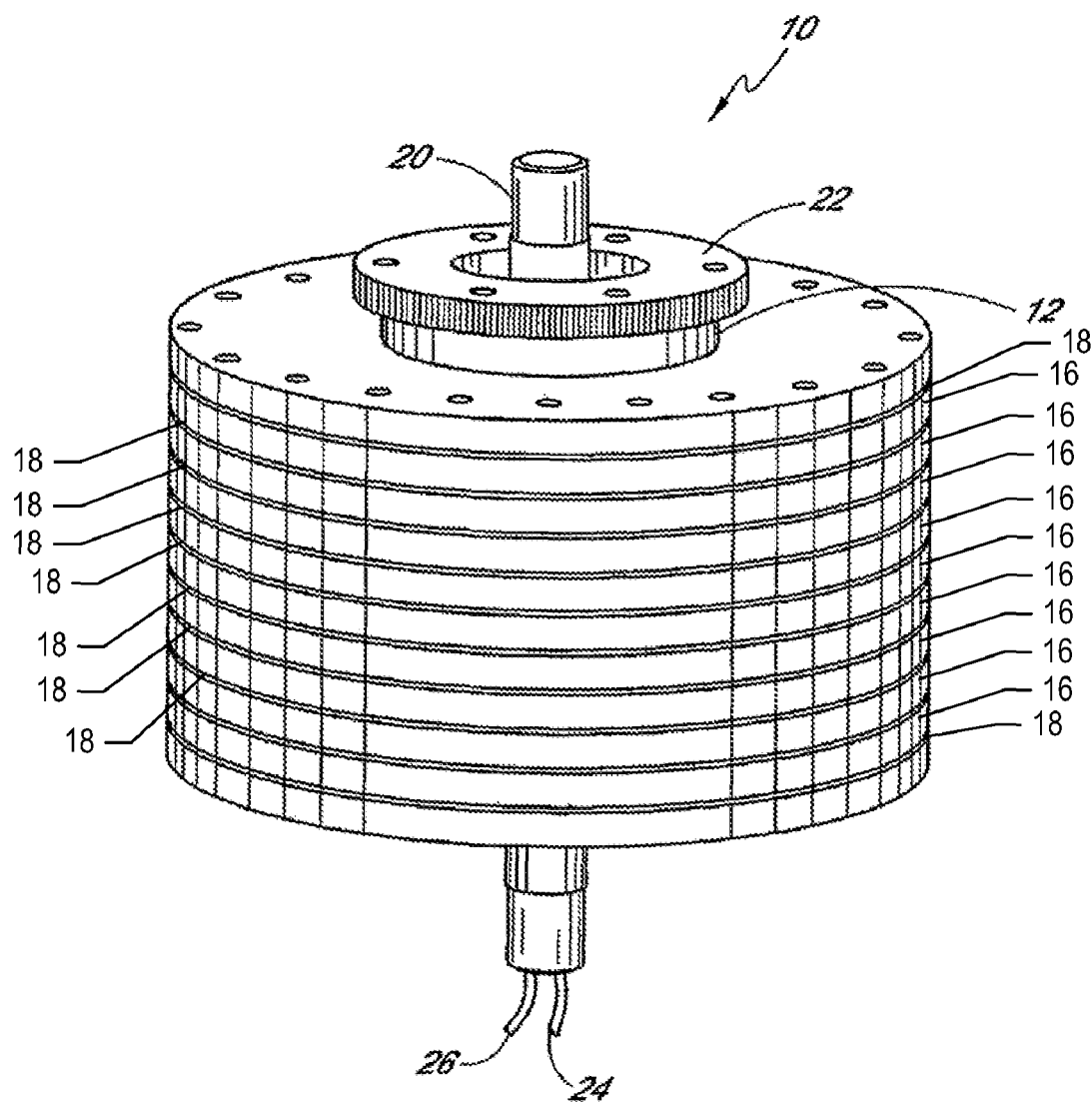
FIG. 1 is a perspective view of a column assembly for use in high speed countercurrent chromatography.

FIG. 1 illustrates a perspective view of one embodiment of a spiral column assembly 10 made in accordance with some aspects of the invention. A hollow column holder shaft 20 is provided with a coaxial planetary gear 22 coupled to an upper flange 12. The planetary gear 22 is configured to be coupled to an identical stationary gear, which is mounted on the central axis of a centrifuge (not illustrated). The gear arrangement provides a synchronous planetary motion of the column with respect to the centrifuge. As a result, a hydrodynamic equilibrium of the solvent system is established such that the two phases within the column are separated along the length of the column. Notably, either phase becomes usable as the mobile phase. As is shown in more detail in FIG. 2, the column is made from a coupled plurality of adjacent plates. Advantageous plate embodiments are illustrated in more detail below with reference to FIGS. 2-4.

The column assembly 10 may be mounted on a rotary frame of any suitable multilayer coil centrifuge as is described in U.S. Pat. No. 4,430,216, previously incorporated by reference in its entirety. In one embodiment, the column assembly 10 is removeably mounted to a mulilayer coil centrifuge manufactured by P.C. Inc. (Potomac, Md.) and retentively engaged by detachable bearing blocks secured to the centrifuge by means of fastening screws. The bearing blocks also serve to counterbalance the column assembly.

Still with reference to FIG. 1, an inlet flow tube 24 and an outlet flow tube 26 may pass through a center bore in the column holder shaft 20 downward and out of the column assembly 10 to exit the complete centrifuge apparatus (not shown), for example at a center hole in an upper plate of the complete centrifuge apparatus and the inlet flow tube 24 and outlet flow tube 26 may be tightly fixed with a pair of clamps (see, for example, the routing shown in U.S. Pat. No. 4,430,216). Advantageously, flow tubes 24 and 26 may be protected with a sheath of flexible tubing such as Tygone (Norton Company, Worcester, Mass.) to prevent direct contact with metal parts in the complete centrifuge apparatus.

Figure 2:
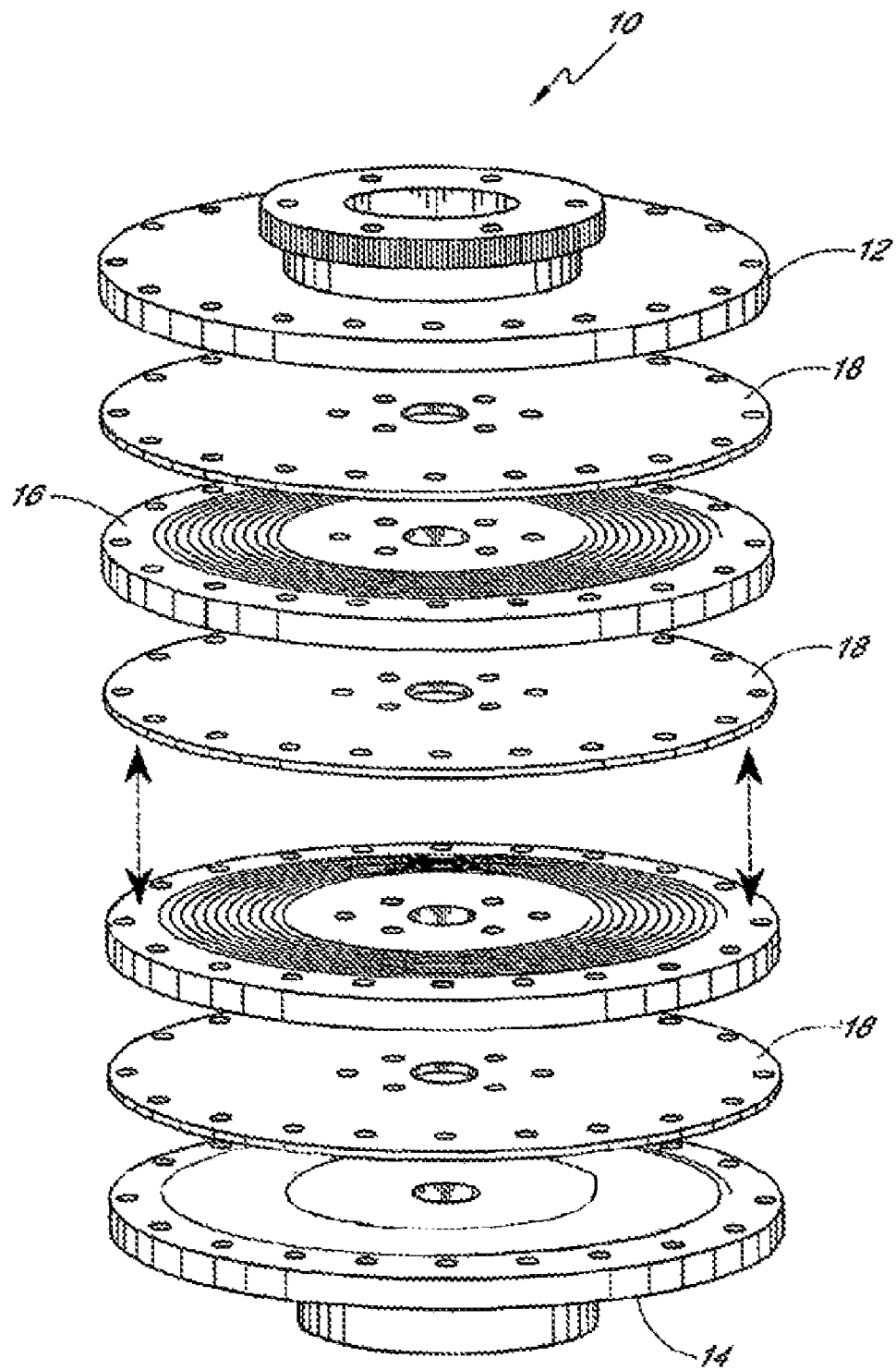
FIG. 2 is an exploded view of the column assembly depicted in FIG. 1.

FIG. 2 is an exploded view of the components of the column assembly illustrated in FIG. 1. The column assembly 10 comprises an upper flange 12 having a gear 22 and a lower flange 14. Disposed between the upper flange 12 and the lower flange 14 are a plurality of fluidly connected separation disks 16a-16b. Alternating between each of the plurality of separation disks 16a-16b is a septum 18a. Another septum 18b is situated between the upper flange 12 and the uppermost separation disk 16a, and yet another septum 18c is situated between the lowermost separation disk 16b and the lower flange 14. The separation disks 16 can be constructed from stainless steel or a plastic such as a PTFE, high density polyethylene, or any other suitable polymer. Advantageously, the separation disk 16 may have a diameter of between 1 cm and 30 cm, and a thickness of between 0.5 and 20 mm. In one embodiment that has been found suitable, the separation disk 16 has a diameter of about 17.5 cm and a thickness of about 4 mm. Preferably, the septum 18 is constructed of PTFE (e.g. Teflon®, E.I. Du Pont, Wilmington, Del.). One of skill in the art would appreciate that the septum 18 can be constructed from any number of suitable non-reactive materials. The construction of the separation disks 16 and septa 18 are described in additional detail below with reference to FIGS. 3, 4A, and 4B.

Figure 3:
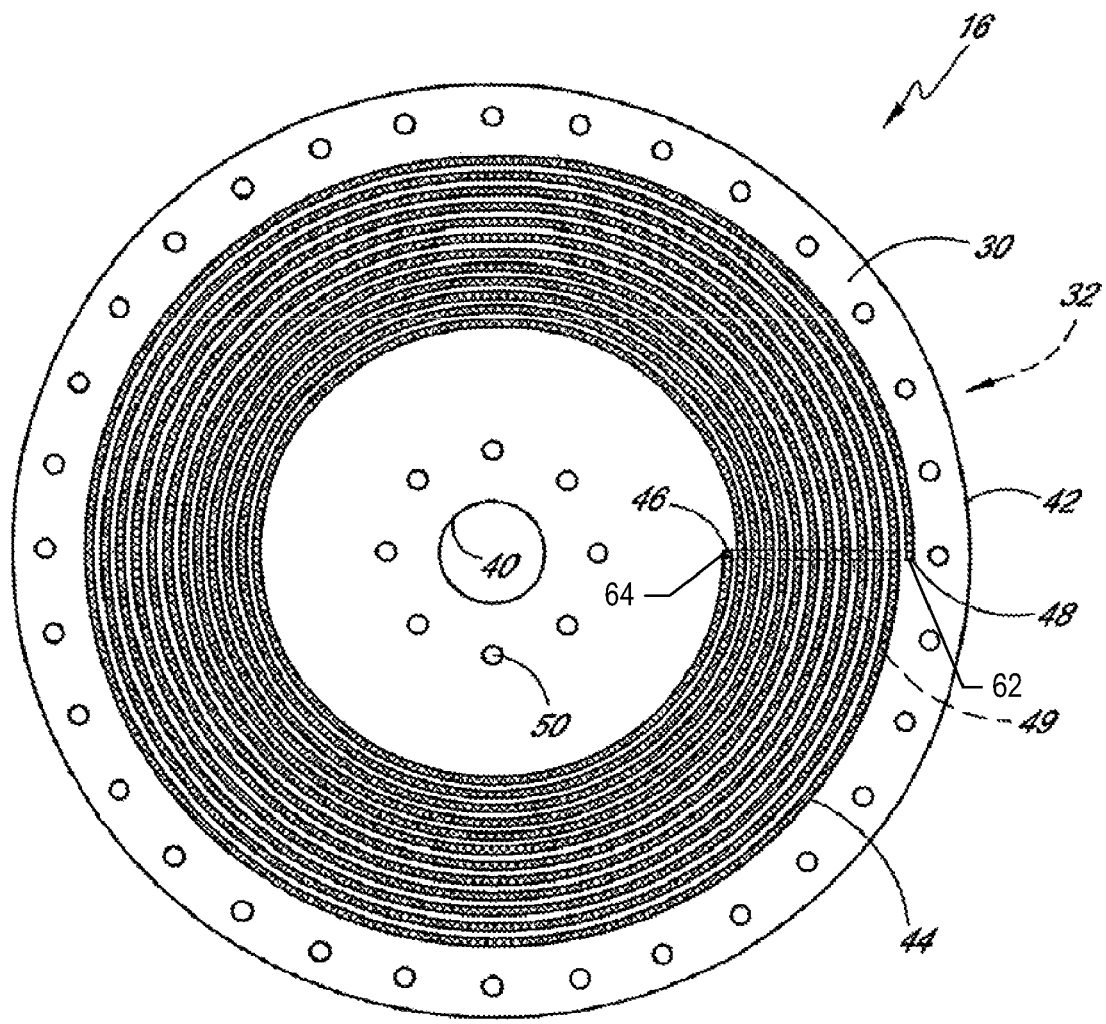
FIG. 3 is a top view of a separation disk with a single spiral channel.

Turning now to FIG. 3, a first embodiment of a separation disk 16 having a first surface 30 and a second opposed surface 32 is illustrated. The separation disk 16 includes an inner edge 40 and an outer edge 42. The separation disk 16 comprises a single spiral flow channel 44 carved, etched, or molded on the surface of the first side 30 of the separation disk 16. The spiral flow channel 44 has an inlet end 46 and an outlet end 48 with fluid flow typically traveling along the path of the spiral channel 44 from the inlet end 46 to the outlet end 48. Advantageously, the spiral channel 44 of one separation disk 16 is serially connected to the spiral channel 44a of another separation disk 16a (not shown) by stacking multiple separation disks 16 adjacent to one another with septa 18 separating each pair. Preferably, the outlet end 48 of the channel 44 connects to the inlet end 46a of the channel 44a on the next adjacent disk 16a (not shown). To accomplish this, the bottom of the outlet end 48 of the channel 44 includes an outer hole 62 (which may be about 1 mm diameter) that is connected to a radial channel 49 grooved or molded into the second opposed surface 32 of the separation disk 16, that extends through the thickness of the separation disk 16. The radial channel 49 grooved within the second opposed surface 32 extends radially inward and substantially aligns with the inlet end 46 of the spiral channel 44 and is physically separated from the inlet end 46 by the material of the separation disk 16. An inner hole 64 in the radial channel 49 is adjacent to a hole in the septum 18 (not shown) that connects to the inlet end 46a of the spiral channel 44a on the next adjacent disk 16a (not shown).

Figure 5:
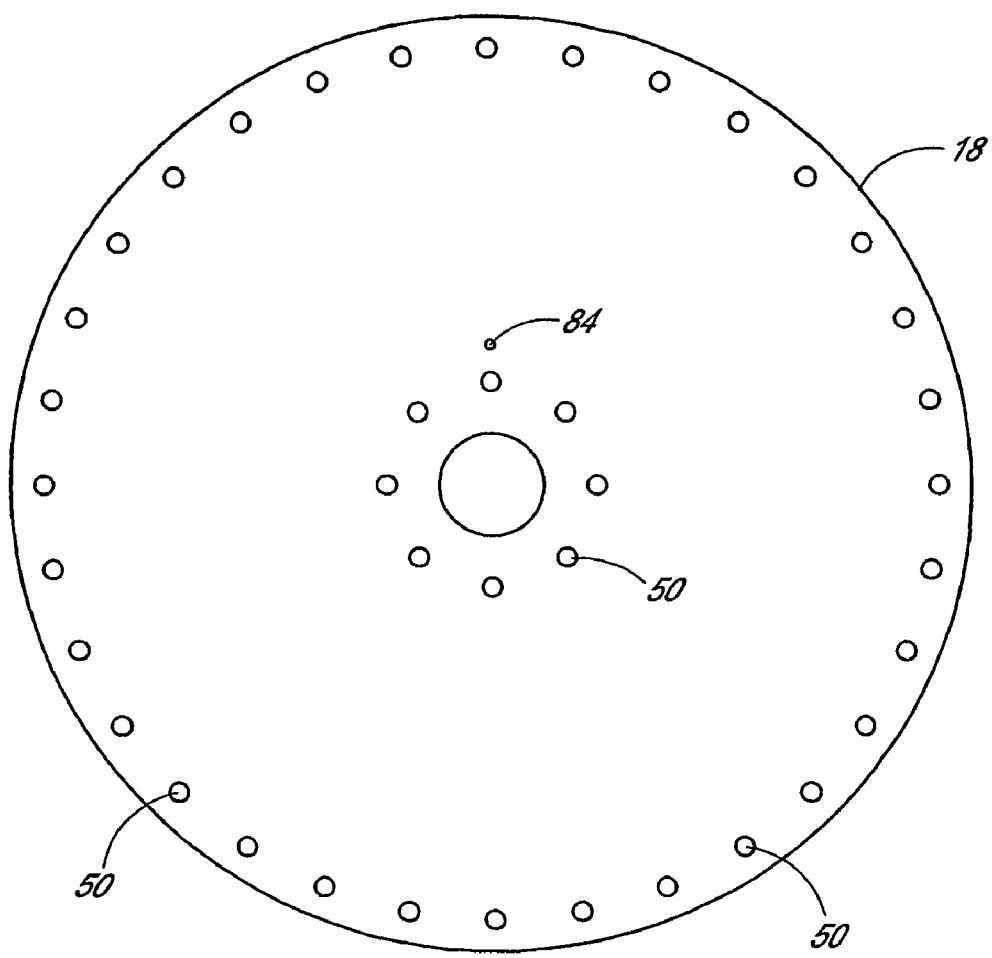
FIG. 5 is a top view of a septum.

To hold the separation disks 16 together in making the whole column assembly 10, each separation disk 16 advantageously includes a plurality of screw holes 50 at regular intervals near both the inner 40 and outer 42 edges of the separation disk 16. In some suitable embodiments, the screw holes 50 are positioned circumferentially at approximately 10 degree spacings for the outer edge 42 and 45 degree spacings for the inner edge 40. Similar holes (not shown) are also made in both the septa 18 and the flanges 12 and 14 as will be described in greater detail with reference to FIGS. 5, 6, and 7.

Figure 4C:
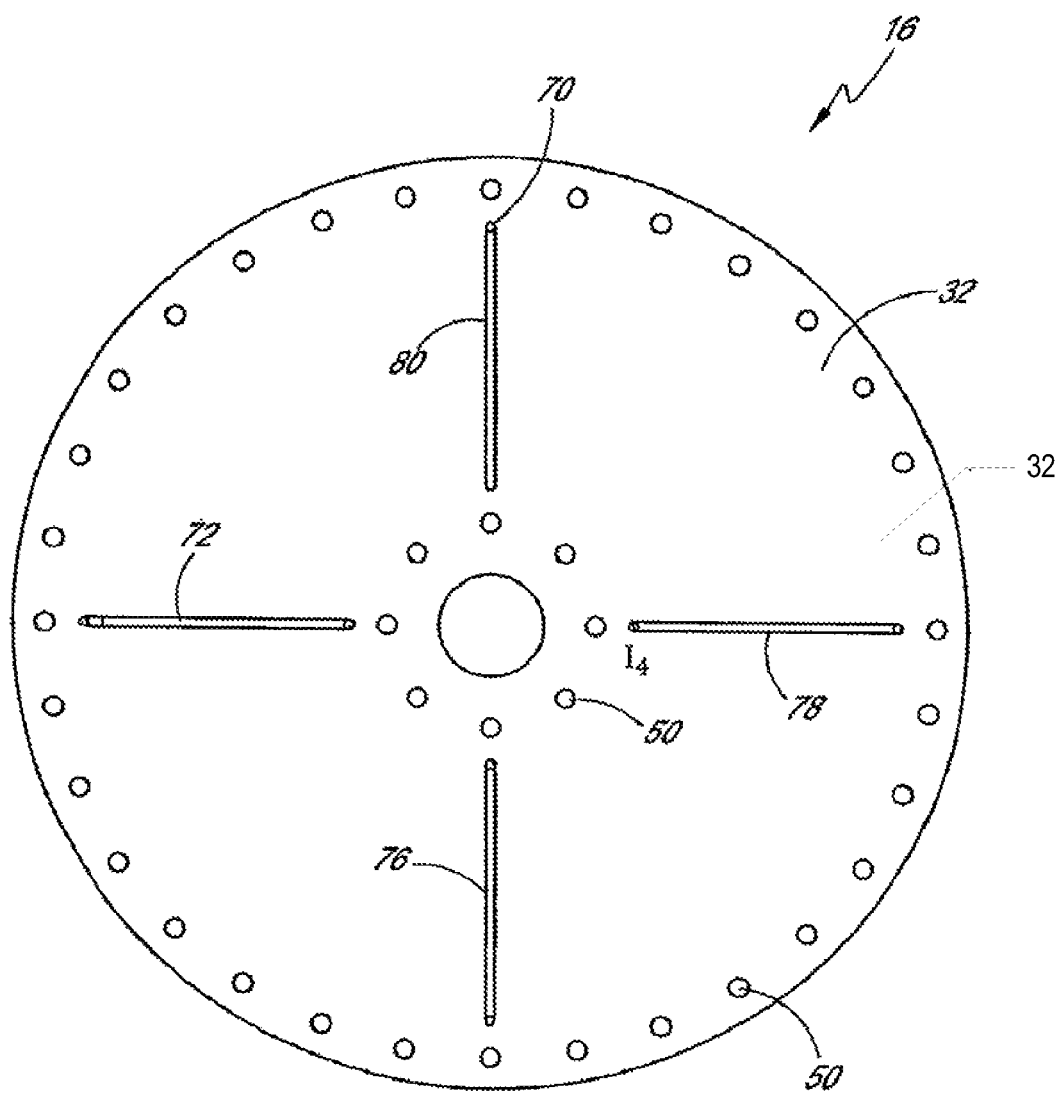
FIG. 4C is a bottom view of a separation disk as illustrated in FIG. 4A.

In a preferred embodiment, multiple interleaved spiral flow channels are incorporated symmetrically around the center of a separation disk 16 so that the spiral pitch is increased as compared to the spiral pitch of a single spiral channel 44 such as is shown in FIG. 3. FIG. 4A is a top view of the first surface 30 of a separation disk 16 having a plurality of interleaved spiral channels 52, 54, 56, and 58. FIG. 4B is a cross section of the separation disk 16 of FIG. 4A, and FIG. 4C is a top plan view of the separation disk 16 of FIGS. 4A and 4B. As illustrated in these Figures, the separation disk 16 has four interconnected spiral channels 52, 54, 56, and 58. However, it will be appreciated that the number of spiral channels can vary. Each channel may be between 0.25 mm and 10 mm wide. Preferably, the width of each channel may be between 0.5 mm and 7 mm wide, with 3 mm having been found suitable in one embodiment. The depth of each channel can likewise vary. Preferably, the depth of each channel is between 0.1 mm and 5 mm, with 2 mm having been found suitable in one embodiment. Depending on the size of the disk, each channel may have a length of between about 250 mm and 5 m. In one advantageous embodiment, the length of each channel is approximately 1 m. It will be appreciated, however, that the length of each channel can vary. Each groove or channel is separated from the next groove or channel by a ridge 60, which may measure approximately 1 mm in width for 3 mm wide channels.

Still with reference to FIG. 4A, each channel 52, 54, 56, and 58 has an inner end denoted I1, I2, I3, and I4 respectively in FIG. 4A. The channels 52, 54, 56, and 58 each begin at their inner ends I1, I2, I3, and I4 and spiral around to their outer ends denoted O1, O2, O3, and O4 respectively in FIG. 4A. In the embodiment of FIG. 4A, each channel 52, 54, 56, and 58 forms 2.75 spiral turns so that the outer end of a given channel is at the same angular location relative to the inner end of the next channel. Thus, as shown in FIG. 4A, O1 is at the same angular orientation as I2, O2 is at the same angular orientation as I3, and O3 is at the same angular orientation as I4.

Connection between the outer end of one spiral channel O1, O2, and O3 and the inner end I2, I3, and I4, respectively of the next spiral channel is made by connecting channels 72, 76, and 78, respectively, that are formed on the second opposed surface 32 of the separation disk 16 as illustrated with dashed lines on FIG. 4A and also on FIG. 4C, which shows a top plan view of the second opposed surface 32. Except for the inner end I1 of the first channel 52 and the outer end O4 of the last channel 58, each end of the channels 52, 54, 56, and 58, have a hole 70 (approximately 1 mm in diameter) through the separation disk 16 which communicates with the end of the connecting channels 72, 76, or 78 on the opposed surface 32 of the separation disk 16.

Referring now to FIGS. 4A, 4B, 4C, and 5, when a sample solution is introduced into the column assembly 10, fluid enters the inner end I1 of the first channel 52 and travels in the direction of the spiral to the outer end O1 of the first channel 52. At this point, the fluid travels through hole 70 to the end of the connecting channel 72 on the opposed surface 32 of the separation disk 16, thereby providing a flow path for the sample to travel from the outer end O1 of the first channel 52 to the radial location of the inner end I2 of the next channel 54. From there the fluid flows through another hole 70 connecting channel 72 and the inner end I2 of the second spiral channel 54. The fluid then travels around to the outer end O2 of the second channel 54, where it passes through a hole 70 to the connecting channel 78 on the opposed surface 32 of the separation disk 16, where it travels radially to the location of the inner end I3 of the third channel 56. This process is repeated through the third channel 56, connecting channel 78, and fourth channel 58 until the fluid emerges at the outer end O4 of the fourth channel 58. At this point, the fluid passes through another hole 70 at the outer end O4 of the fourth channel 58 and through connecting channel 80 to the radial position of inner end I1 where the flow started. However, no hole through the separation disk 16 to the inner end I1 of the first channel 52 is provided. Rather, an interdisk connection hole 84 in the septum 18 is positioned to coincide with the location of the inner end I1 of the first channel 52 on one separation disk 16 and with the inner end I1a of the first channel 52a on the next adjacent separation disk 16a (not shown). The interdisk connection hole 84 conducts the fluid from the connecting channel 80 of the separation disk 16 to the inner end I1a of the next adjacent separation disk 16a (not shown). Thus, in a series of adjacent separation disks 16a-16b as shown in FIG. 1, fluid passes from the outer end O4 of the fourth channel 58 on one separation disk 16a to the inner end I1a of the first channel 52a on the next separation disk 16b (not shown).

In operation, the pitch of each additional spiral on a separation disk 16 may increase markedly as compared to the pitch of a single spiral channel, assuming that the volume of fluid contained in the single spiral channel is essentially the same as the volume of fluid contained in the multiple spirals. For example, when a separation disk 16 with a diameter of about 17.5 cm includes four spiral channels, the pitch of each spiral may become as large as 16 mm (three times that of the single spiral channel).

Figure 6:
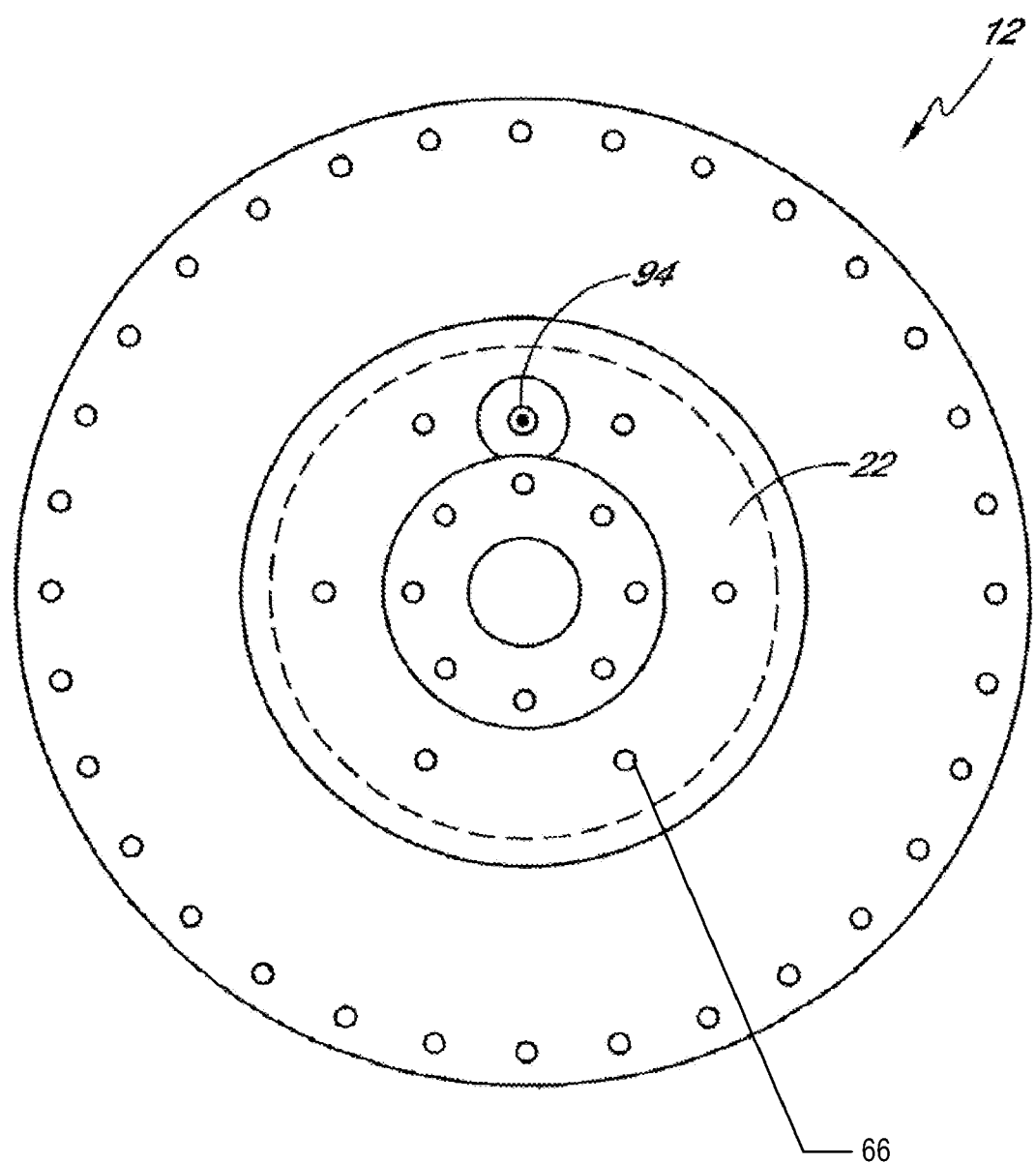
FIG. 6 is a top view of an upper flange and gear.
Figure 7:
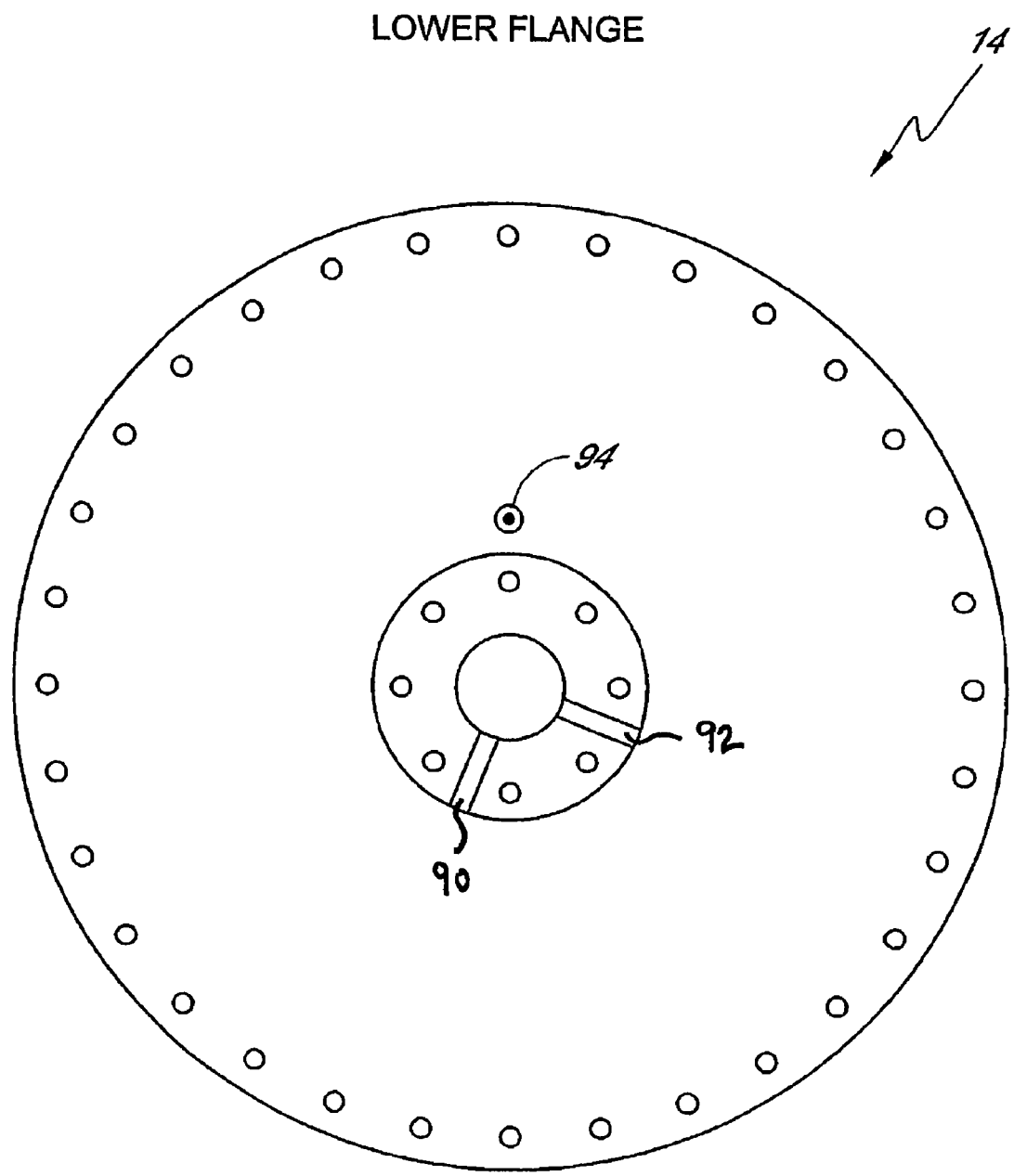
FIG. 7 is a bottom view of a lower flange.

One embodiment of the flanges which are placed on the top and bottom of the stack of separation disks 16 of FIG. 1 is shown in FIGS. 6 and 7. The upper flange 12 (FIG. 6) is equipped with a gear 22 which engages with a stationary gear on the HSCCC centrifuge (not shown). FIG. 7 depicts the lower flange 14 which has two screw holes 90, 92 positioned substantially 90 degrees apart circumferentially for tightly fixing the column assembly 10 against the column holder shaft (0.9 inch diameter). Both the upper and lower flanges 12, 14 each have an inlet/outlet hole 94 which fits to an adapter (not shown) with a screw thread. They also have a set of screw holes 66 located at regular intervals around the circumference near the outer and inner edges of each septum 18 in alignment with the screw holes 50 of the separation disks 16 and septa 18. In preferred embodiments, the screw holes 66 are positioned circumferentially at approximately 10 degree spacings for the outer edge and 45 degree spacings for the inner edge.

It has been observed that the use of a rectangular spiral channel embedded in a solid separation disk 16 as described above enhances the retention of the stationary phase for viscous, low interfacial tension two-phase solvent systems. Accordingly, in one embodiment, a column assembly 10 having a separation disk 16 comprising at least one rectangular spiral channel 44 embedded in the separation disk 16 is provided. The rectangular spiral channel configuration has a number of advantages over the prior art. For example, the rectangular spiral channel is useful for separating biopolymers such as proteins, DNA, RNA, polysaccharides, and cell particles. Additionally, this channel design ensures reliable retention of the stationary phase for polar or low interfacial tension solvent systems such as the 1-butanol/water system to separate bioactive compounds including peptides. Similarly, the rectangular design provides an improved stationary phase retention against emulsification.

Example

A suitable highly viscous, low interfacial two-phase solvent system is thoroughly equilibrated in a separatory funnel at room temperature and the two phases are separated before use. The sample solution is prepared by dissolving the sample in a proper volume (e.g. 1-5 ml) of the upper and/or lower phase of the solvent system. The spiral column assembly is first entirely filled with the stationary phase (upper or lower phase), followed by sample injection through the sample port The apparatus is rotated at 800 rpm while the mobile phase is eluted through the column at a desired flow rate. The separation may be repeated by changing the direction of the revolution and/or elution mode (i.e., head to tail and tail to head), although it is expected that the best result would be obtained by eluting the lower phase from the internal terminal toward the external terminal of the spiral channel at tail to head elution mode or the upper phase from the opposite direction in the head to tail mode.

The effluent from the outlet of the column is continuously monitored through a uv detector and fractionated into test tubes for later analysis.

In accordance with the foregoing, certain embodiments of the invention provide an improved column design for use in high speed countercurrent chromatography, which increases the retention of the stationary phase and increases efficiency of the chromatographic system. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A countercurrent chromatography apparatus comprising:
    a column assembly comprising a plurality of plates, each of the plurality of plates defining an inlet, an outlet, and a plurality of interleaved spiral flow channels, the inlet being in fluid flow communication with one of the plurality of interleaved spiral flow channels and the outlet being in fluid flow communication with another of the plurality of interleaved spiral flow channels, each of the plurality of interleaved, spiral flow channels in one of the plurality of plates is in fluid flow communication with another one of the plurality of interleaved spiral flow channels in the same one of the plurality of plates.

2. The countercurrent chromatography apparatus of claim 1, further comprising a septa positioned on either side of the each of the plurality of plates, wherein the septa includes a hole positioned to establish a fluid connection between one of the plurality of interleaved spiral flow channels in one of said plurality of plates and another one of the plurality of interleaved spiral flow channels in another one of said plurality of plates.

3. The countercurrent chromatography apparatus of claim 1, further comprising an upper flange and a lower flange, the plurality of plates being interposed between the upper flange and the lower flange wherein at least the upper flange or the lower flange includes a gear.

4. A plate for use in countercurrent chromatography comprising:
    a first surface defining an inlet and an outlet and a second opposed surface;
    a plurality of interleaved spiral flow channels defined along the first surface, wherein the inlet is in fluid flow communication with one of the plurality of interleaved spiral flow channels and the outlet is in fluid flow communication with another one of the plurality of interleaved spiral flow channels, each of the plurality of interleaved spiral flow channels having an inner end and an outer end; and
    at least one flow path to establish fluid flow communication between an outer end of at least one of said interleaved spiral flow channels with an inner end of another one of said interleaved spiral flow channels.

5. The plate of claim 4, wherein said plurality of interleaved spiral flow channels comprises grooves formed in said first surface.

6. The plate of claim 5, wherein said flow path comprises a groove formed in said second opposed surface.

7. The plate of claim 6, wherein said groove extends substantially radially from a point closer to the outer surface of said second opposed surface to a point close to the central axis of said second opposed surface.

8. The plate of claim 4, wherein said plurality of interleaved spiral flow channels have a substantially rectangular cross section.

9. The plate of claim 5, wherein said plurality of interleaved spiral flow channels comprises four interleaved spiral grooves in said first surface.

10. The plate of claim 6, comprising four interleaved spiral grooves in said first surface and four radially extending grooves in said second surface for establishing fluid flow communication between each of the four interleaved spiral grooves.

11. A countercurrent chromatography apparatus comprising:
    a column assembly having a plurality of coupled separation disks, each of said coupled separation disks defining an inlet and an outlet, and further defining a plurality of interleaved spiral flow channels, with the inlet being in fluid flow communication with one of the plurality of interleaved spiral flow channels and outlet being in fluid flow communication with another one of the plurality of interleaved spiral flow channels, at least one of the plurality of interleaved spiral flow channels being in fluid flow communication with at least another one of the plurality of interleaved spiral flow channels wherein each of said plurality of interleaved spiral flow channels comprises an inner end and an outer end, wherein the inner end of each of the plurality of interleaved spiral flow channels is closer to a central axis defined through each of the plurality of said separation disks than said outer end of each of the plurality of interleaved spiral flow channels, and wherein the outer end of at least one of said interleaved spiral flow channels is in fluid flow communication with the inner end of another one of said interleaved spiral flow channels.

12. The apparatus of claim 11, wherein the outer end of at least one of the plurality of interleaved spiral flow channels of one of the plurality of coupled separation plates is in fluid communication with the inner end of another one of a plurality of interleaved spiral flow channels in another plurality of coupled separation disks.

13. A countercurrent chromatography apparatus comprising:
- a series of coupled plates;
- a groove means in said plates for routing fluid through a plurality of interleaved spiral flow paths, wherein each of said plurality of interleaved spiral flow paths comprises a first end and a second end, wherein said first ends are closer to a central axis of said plates than said second end and wherein the second end of at least one of said plurality of interleaved spiral flow paths is in fluid flow communication with the first end another one of said plurality of interleaved spiral flow paths, wherein the first end of one of the plurality of interleaved spiral flow channels is in fluid flow communication with an inlet and the second end of another one of the plurality of interleaved spiral flow channels is in fluid flow communication with an outlet.

14. The apparatus of claim 13, wherein said groove means is provided on first and second sides of at least one of said plates.

15. The apparatus of claim 14, wherein said groove means on said first side of at least one plate is a plurality of spiral flow paths and said groove means on said second means on said second side of at least one plate is substantially radial flow path connecting the outer end of at least one spiral flow path to the inner end of a different one spiral flow path.

* * * * *